United States Patent [19]

Scrima et al.

[11] Patent Number: 5,457,199
[45] Date of Patent: Oct. 10, 1995

[54] PIPERIDINE COMPOUNDS FOR USE AS STABILIZERS FOR ORGANIC MATERIALS

[75] Inventors: Roberto Scrima, Bologna; Graziano Zagnoni, Vergato, both of Italy

[73] Assignee: Ciba-Geigy Corporation, Ardsley, N.Y.

[21] Appl. No.: 273,292

[22] Filed: Jul. 11, 1994

[30] Foreign Application Priority Data

Jul. 16, 1993 [IT] Italy .................. MI93A1581

[51] Int. Cl.$^6$ .................. C07D 251/54; C07D 251/52
[52] U.S. Cl. .................. 544/198; 544/6; 544/70; 544/113; 544/209; 544/212; 544/219
[58] Field of Search .................. 544/60, 70, 113, 544/198, 209, 212, 219, 208

[56] References Cited

U.S. PATENT DOCUMENTS

| | | | |
|---|---|---|---|
| 4,102,858 | 7/1978 | Minagawa et al. | 260/45.8 |
| 4,108,829 | 8/1978 | Cassandrini et al. | 260/45.8 |
| 4,263,434 | 4/1981 | Cassandrini et al. | 544/198 |
| 4,883,831 | 11/1989 | Nelson et al. | 524/100 |
| 4,883,860 | 11/1989 | Nelson et al. | 524/98 |
| 5,059,689 | 10/1991 | Rody et al. | 544/198 |

FOREIGN PATENT DOCUMENTS

| | | |
|---|---|---|
| 0328024 | 8/1989 | European Pat. Off. |
| 0122479 | 7/1984 | Japan .................. 544/198 |
| 1176662 | 8/1986 | Japan .................. 544/198 |
| 2134112 | 8/1984 | United Kingdom . |
| 2202853 | 10/1988 | United Kingdom . |

OTHER PUBLICATIONS

Research Disclosure 1990, 31429, pp. 474–480.

*Primary Examiner*—Yogendra N. Gupta
*Attorney, Agent, or Firm*—Luther A. R. Hall

[57] ABSTRACT

The present invention relates to novel piperidine compounds of the formula (I)

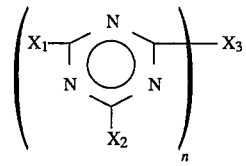

in which $X_1$, $X_2$, $X_3$ and n are as defined in the text.

The compounds of the invention can be used as light stabilizers, heat stabilizers and oxidation stabilizers for organic materials, in particular synthetic polymers.

6 Claims, No Drawings

PIPERIDINE COMPOUNDS FOR USE AS STABILIZERS FOR ORGANIC MATERIALS

The present invention relates to novel piperidine compounds, to their use as light stabilizers, heat stabilizers and oxidation stabilizers for organic materials, in particular synthetic polymers, and to the organic materials thus stabilized.

U.S. Pat. Nos. 4,883,831 and 4,883,860 claim the stabilization of synthetic polymers with certain piperidine esters of triazinylamino acids.

In U.S. Pat. No. 4,102,858, certain piperidine esters of aspartic acid are reported as stabilizers for synthetic polymers.

The present invention relates to novel compounds of the formula (I)

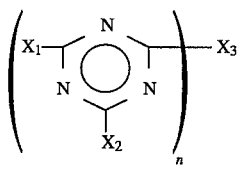

in which $X_1$ and $X_2$ which can be identical or different are a group of the formula (II)

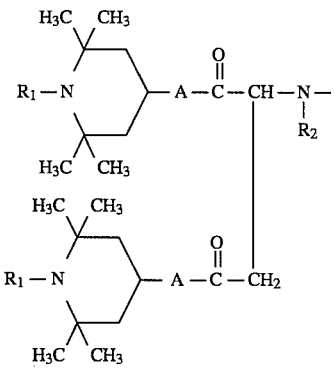

in which $R_1$ is hydrogen, $C_1$–$C_8$alkyl, O, OH, $CH_2CN$, $C_1$–$C_{18}$alkoxy, $C_5$–$C_{12}$cycloalkoxy, $C_3$–$C_6$-alkenyl, $C_7$–$C_9$phenylalkyl unsubstituted or mono-, di- or tri-substituted on the phenyl by $C_1$–$C_4$alkyl; or aliphatic $C_1$–$C_8$acyl, $R_2$ is hydrogen, $C_1$–$C_{18}$alkyl, $C_5$–$C_{12}$cycloalkyl unsubstituted or mono-, di- or tri-substituted by $C_1$–$C_4$alkyl; $C_7$–$C_9$phenylalkyl unsubstituted or mono-, di- or tri-substituted on the phenyl by $C_1$–$C_4$alkyl; tetrahydrofurfuryl or a group of the formula (III)

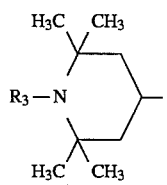

where $R_3$ is as defined for $R_1$ or $C_2$–$C_4$alkyl substituted in the 2-, 3- or 4-position by $C_1$–$C_8$alkoxy, by di($C_1$–$C_4$alkyl)amino or by a group of the formula (IV)

where $Q_1$ is a direct bond, —O—, —$CH_2$—, —$CH_2CH_2$— or

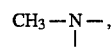

and A is —O— or

with $R_4$ being hydrogen or $C_1$–$C_{12}$alkyl, or $X_1$ and $X_2$ are a group of the formula (IV) or one of the groups of the formulae (Va)–(Ve)

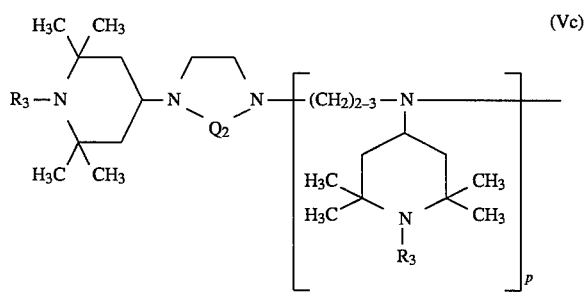

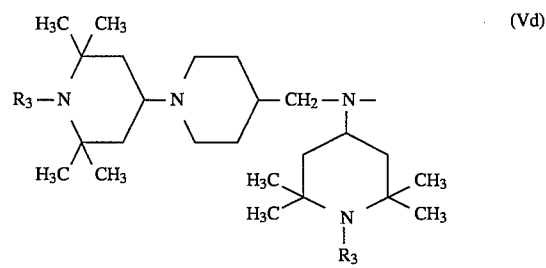

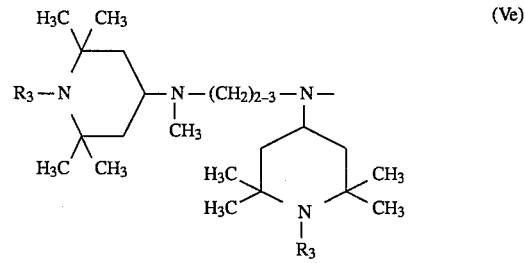

in which $R_3$ is as defined above, $R_5$, $R_6$ and $R_7$ which can be identical or different are as defined for $R_2$, or $R_7$ is also $C_3$–$C_{18}$alkenyl or phenyl unsubstituted or mono-, di- or tri-substituted by $C_1$–$C_4$alkyl or $C_1$–$C_4$alkoxy;

$Q_2$ is —CO—, —CH$_2$CH$_2$—, —COCO—, —CH$_2$CO— or —COCH$_2$CO— and p is zero or 1, n is 1, 2, 3 or 4 and, if n is 1, $X_3$ is as defined for $X_1$ and $X_2$, and, if n is 2, $X_3$ is one of the groups of the formulae (VIa)–(VIc)

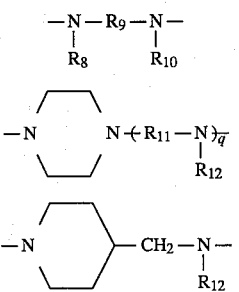

in which $R_8$, $R_{10}$ and $R_{12}$ which can be identical or different are as defined for $R_2$, or $R_8$ and $R_{10}$ are also a group of the formula (VII)

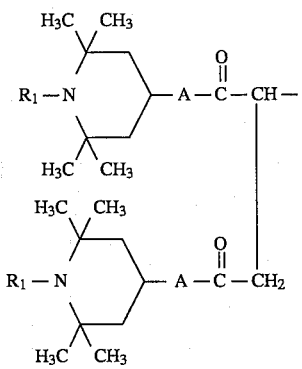

with $R_1$ and A as defined above, $R_9$ is $C_2$–$C_{12}$alkylene, $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene), phenylenedi($C_1$–$C_4$alkylene) or $C_4$–$C_{12}$alkylene interrupted by a 1,4-piperazinediyl group or by 1, 2 or 3 oxygen atoms or by 1 or 2

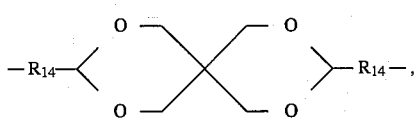

groups, where $R_{13}$ is as defined for $R_2$ or is aliphatic $C_1$–$C_{12}$acyl or ($C_1$–$C_{12}$alkoxy)carbonyl, or $R_9$ is also a group

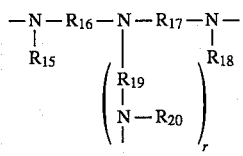

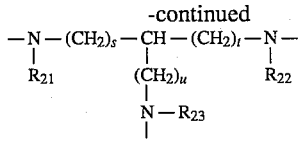

$R_{11}$ and $R_{14}$ are $C_2$–$C_6$alkylene and q is zero or 1, and if n is 3, $X_3$ is a group of the formula (VIIIa) or (VIIIb)

in which $R_{15}$, $R_{18}$, $R_{20}$, $R_{21}$, $R_{22}$ and $R_{23}$ which can be identical or different are as defined above for $R_8$ and $R_{10}$, $R_{16}$, $R_{17}$ and $R_{19}$ which can be identical or different are $C_2$–$C_6$alkylene, r and u are zero or 1, and s and t which can be identical or different are integers from 2 to 6, and, if n is 4, $X_3$ is a group of the formula (IX)

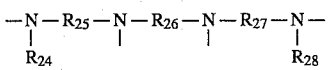

in which $R_{24}$ and $R_{28}$ which can be identical or different are as defined above for $R_8$ and $R_{10}$, and $R_{25}$, $R_{26}$ and $R_{27}$ which can be identical or different are $C_2$–$C_6$alkylene, with the proviso that at least one group of the formula (II) or of the formula (VII) is present in the compounds of the formula (I).

Examples of alkyl having not more than 18 carbon atoms are methyl, ethyl, propyl, iso-propyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

Examples of $C_2$–$C_4$alkyl substituted by $C_1$–$C_8$alkoxy, preferably by $C_1$–$C_4$alkoxy, in particular methoxy or ethoxy, are 2-methoxyethyl, 2-ethoxyethyl, 3-methoxypropyl, 3-ethoxypropyl, 3-butoxypropyl, 3-octoxypropyl and 4-methoxybutyl.

Examples of $C_2$–$C_4$alkyl substituted by di($C_1$–$C_4$alkyl)amino, preferably by dimethylamino or diethylamino, are 2-dimethylaminoethyl, 2-diethylaminoethyl, 3-dimethylaminopropyl, 3-diethylaminopropyl, 3-dibutylaminopropyl and 4-diethylaminobutyl.

Preferred examples of $C_2$–$C_4$alkyl substituted by a group of the formula (IV) are the groups

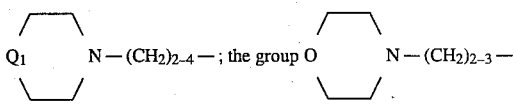

is particularly preferred.

Examples of alkoxy having not more than 18 carbon atoms are methoxy, ethoxy, propoxy, isopropoxy, butoxy, isobutoxy, pentoxy, isopentoxy, hexoxy, heptoxy, octoxy, decyloxy, dodecyloxy, tetradecyloxy, hexadecyloxy and octadecyloxy. Preferred examples of $R_1$ and $R_3$ are $C_6$–$C_{12}$alkoxy, in particular heptoxy and octoxy.

Examples of $C_5$–$C_{12}$cycloalkyl unsubstituted or mono-, di- or tri-substituted by $C_1$–$C_4$alkyl are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl. Unsubstituted or substituted cyclohexyl is preferred.

Examples of $C_5$–$C_{12}$cycloalkoxy $R_1$ and $R_3$ are cyclopentoxy, cyclohexoxy, cycloheptoxy, cyclooctoxy, cyclodecyloxy and cyclododecyloxy. Cyclopentoxy and cyclohexoxy are preferred.

Examples of alkenyl having not more than 18 carbon atoms are allyl, 2-methylallyl, butenyl, hexenyl, undecenyl and octadecenyl. Alkenyls in which the carbon atom in the 1-position is saturated are preferred; allyl is particularly preferred.

Representative examples of phenyl mono-, di- or tri-substituted by $C_1$–$C_4$alkyl or $C_1$–$C_4$alkoxy are methylphenyl, dimethylphenyl, trimethylphenyl, t-butylphenyl, di-t-butylphenyl, 3,5-di-t-butyl-4-methylphenyl, methoxyphenyl, ethoxyphenyl and butoxyphenyl.

Examples of $C_7$–$C_9$phenylalkyl unsubstituted or mono-, di- or tri-substituted on the phenyl by $C_1$–$C_4$alkyl are benzyl, methylbenzyl, dimethylbenzyl, trimethylbenzyl, 2-butylbenzyl and 2-phenylethyl. Benzyl is preferred.

Representative examples of aliphatic acyl having not more than 12 carbon atoms are acetyl, propionyl, butyryl, isobutyryl, pentanoyl, hexanoyl, heptanoyl, octanoyl, 2-ethylhexanoyl, decanoyl, undecanoyl, dodecanoyl, acryloyl, crotonyl and 10-undecenoyl. $C_1$–$C_8$Alkanoyl and $C_3$–$C_8$alkenoyl are particularly preferred.

Examples of alkylene having not more than 12 carbon atoms are ethylene, propylene, trimethylene, 2-methyltrimethylene, 2,2-dimethyltrimethylene, tetramethylene, pentamethylene, hexamethylene, trimethylhexamethylene, octamethylene, decamethylene and dodecamethylene.

A preferred example of $C_4$–$C_{12}$alkylene $R_9$ interrupted by a 1,4-piperazinediyl group is the group

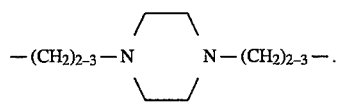

Examples of $C_4$–$C_{12}$alkylene interrupted by 1, 2 or 3 oxygen atoms are 4-oxaheptane-1,7-diyl, 4,7-dioxadecane-1,10-diyl, 4,9-dioxadodecane-1,12-diyl and 4,7,10-trioxatridecane-1,13-diyl.

Representative examples of $C_4$–$C_{12}$alkylene $R_9$ interrupted by 1 or 2

groups are the groups

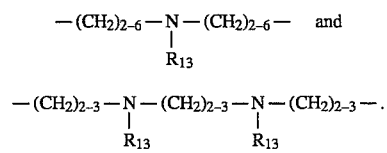

Representative examples of groups having 1 or 2 $C_5$–$C_7$cycloalkylene groups are cyclohexylene, methylcyclohexylene, cyclohexylenedimethylene, methylenedicyclohexylene and the group

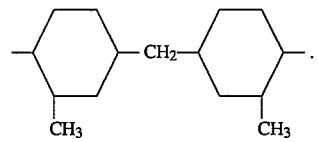

Phenylenedimethylene is the preferred example of phenylenedi($C_1$–$C_4$alkylene).

Preferred definitions of $R_1$ and $R_3$ are hydrogen, $C_1$–$C_4$alkyl, OH, $C_6$–$C_{12}$alkoxy, $C_5$–$C_8$cycloalkoxy, allyl, benzyl or acetyl, in particular hydrogen or methyl.

Those compounds of the formula (I) are preferred in which $X_1$ and $X_2$ which can be identical or different are a group of the formula (II) in which $R_2$ is hydrogen, $C_1$–$C_{16}$alkyl, $C_5$–$C_8$cycloalkyl unsubstituted or mono-, di- or tri-substituted by $C_1$–$C_4$alkyl; benzyl unsubstituted or mono-, di- or tri-substituted on the phenyl by $C_1$–$C_4$alkyl; tetrahydrofurfuryl, a group of the formula (III), $C_2$–$C_3$alkyl substituted in the 2- or 3-position by $C_1$–$C_4$alkoxy, by di-($C_1$–$C_4$alkyl)amino or by a group of the formula (IV), where $Q_1$ is a direct bond, —O—, —$CH_2$— or —$CH_2CH_2$—, and A is —O— or

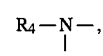

with $R_4$ being hydrogen or $C_1$–$C_{10}$alkyl, or $X_1$ and $X_2$ are a group of the formula (IV) or one of the groups of the formulae (Va)–(Ve), in which $R_5$, $R_6$ and $R_7$ which can be identical or different are as defined for $R_2$, or $R_7$ is also $C_3$–$C_{12}$alkenyl or phenyl unsubstituted or mono-, di- or tri-substituted by $C_1$–$C_4$alkyl or $C_1$–$C_4$alkoxy, $Q_2$ is —CO—, —$CH_2CH_2$—, —COCO— or —COCH$_2$CO—, p is zero or 1 and n is 1, 2, 3 or 4, and, if n is 1, $X_3$ is as defined for $X_1$ and $X_2$, and, if n is 2, $X_3$ is one of the groups of the formulae (VIa)–(VIc) in which $R_8$, $R_{10}$ and $R_{12}$ which can be identical or different are as defined above for $R_2$ or $R_8$ and $R_{10}$ are also a group of the formula (VII), $R_9$ is $C_2$–$C_{10}$alkylene, cyclohexylene, cyclohexylenedimethylene, methylenedicyclohexylene, phenylenedimethylene, $C_4$–$C_{10}$alkylene interrupted by a 1,4-piperazinediyl group or by 1, 2 or 3 oxygen atoms or by 1 or 2

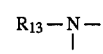

groups, where $R_{13}$ is as defined above for $R_2$ or is aliphatic $C_1$–$C_8$acyl or ($C_1$–$C_8$alkoxy)carbonyl, or $R_9$ is also a group

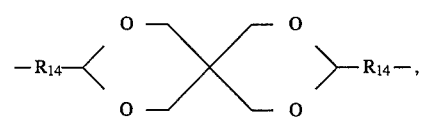

$R_{11}$ and $R_{14}$ are $C_2$–$C_4$alkylene and q is zero or 1, and, if n is 3, $X_3$ is a group of the formula (VIIIa) or (VIIIb), in which $R_{15}$, $R_{18}$, $R_{20}$, $R_{21}$, $R_{22}$ and $R_{23}$ which can be identical or different are as defined above for $R_8$ and $R_{10}$, $R_{16}$, $R_{17}$ and $R_{19}$ which can be identical or different are $C_2$–$C_4$alkylene, r and u are zero or 1 and s and t which can be identical or different are integers from 3 to 6 and, if n is 4, $X_3$ is a group of the formula (IX) in which $R_{24}$ and $R_{28}$ which can be identical or different are as defined above for $R_8$ and $R_{10}$, and $R_{25}$, $R_{26}$ and $R_{27}$ which can be identical or different are $C_2$–$C_4$alkylene, with the proviso that at least one group of the formula (II) or of the formula (VII) is present in the compounds of the formula (I).

Those compounds of the formula (I) are particularly preferred in which $X_1$ and $X_2$ which can be identical or different are a group of the formula (II), where $R_2$ is hydrogen, $C_1$–$C_{14}$alkyl, cyclohexyl unsubstituted or mono-, di- or tri-substituted by $C_1$–$C_4$alkyl; benzyl, tetrahydrofurfuryl, a group of the formula (III), $C_2$–$C_3$alkyl substituted in the 2- or 3-position by methoxy, by ethoxy, by dimethylamino, by diethylamino or by a 4-morpholinyl group, and A is —O— or

with $R_4$ being hydrogen or $C_1$–$C_8$alkyl, or $X_1$ and $X_2$ are a 4-morpholinyl group or one of the groups of the formulae (Va)–(Ve) in which $R_5$, $R_6$ and $R_7$ which can be identical or different are as defined above for $R_2$, or $R_7$ is also $C_3$–$C_{11}$alkenyl or phenyl, $Q_2$ is —CO—, —CH$_2$CH$_2$— or —COCO—, p is zero or 1 and n is 1, 2, 3 or 4, and if n is 1, $X_3$ is as defined above for $X_1$ and $X_2$, and, if n is 2, $X_3$ is one of the groups of the formulae (VIa)–(VIc) in which $R_8$, $R_{10}$ and $R_{12}$ which can be identical or different are as defined above for $R_2$, or $R_8$ and $R_{10}$ are also a group of the formula (VII), $R_9$ is $C_2$–$C_8$alkylene, cyclohexylenedimethylene, methylenedicyclohexylene or phenylenedimethylene, $C_4$–$C_{10}$alkylene interrupted by a 1,4-piperazinediyl group or by 1, 2 or 3 oxygen atoms or by 1 or 2

groups, where $R_{13}$ is as defined above for $R_2$ or is aliphatic $C_1$–$C_4$acyl or ($C_1$–$C_4$alkoxy)carbonyl, or $R_9$ is also a group

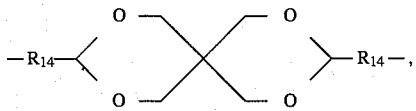

$R_{11}$ and $R_{14}$ are $C_2$–$C_4$alkylene and q is zero or 1, and, if n is 3, $X_3$ is a group of the formula (VIIIa) or (VIIIb) in which $R_{15}$, $R_{18}$, $R_{20}$, $R_{21}$, $R_{22}$ and $R_{23}$ which can be identical or different are as defined above for $R_8$ and $R_{10}$, $R_{16}$, $R_{17}$ and $R_{19}$ which can be identical or different are $C_2$–$C_4$alkylene, r and u are zero or 1 and s and t which can be identical or different are integers from 3 to 5, and, if n is 4, $X_3$ is a group of the formula (IX) in which $R_{24}$ and $R_{28}$ which can be identical or different are as defined above for $R_8$ and $R_{10}$, and $R_{25}$, $R_{26}$ and $R_{27}$ which can be identical or different are $C_2$–$C_4$alkylene, with the proviso that at least one group of the formula (II) or of the formula (VII) is present in the compounds of the formula (I).

Those compounds of the formula (I) are of special interest in which $X_1$ and $X_2$ which can be identical or different are a group of the formula (II), where $R_2$ is hydrogen, $C_1$–$C_{12}$alkyl, cyclohexyl or a group of the formula (III) and A is —O— or

with $R_4$ being hydrogen or $C_1$–$C_4$alkyl, or $X_1$ and $X_2$ are a 4-morpholinyl group or one of the groups of the formulae (Va)–(Ve) in which $R_5$, $R_6$ and $R_7$ which can be identical or different are as defined above for $R_2$, $Q_2$ is —CO— or —CH$_2$CH$_2$—, p is zero or 1 and n is 1, 2, 3 or 4, and, if n is 1, $X_3$ is as defined above for $X_1$ and $X_2$, and, if n is 2, $X_3$ is one of the groups of the formulae (VIa)–(VIc) in which $R_8$, $R_{10}$ and $R_{12}$ which can be identical or different are as defined above for $R_2$, or $R_8$ and $R_{10}$ are also a group of the formula (VII), $R_9$ is $C_2$–$C_6$alkylene, cyclohexylenedimethylene, methylenedicyclohexylene, $C_6$–$C_{10}$alkylene interrupted by a 1,4-piperazinediyl group or by 2 or 3 oxygen atoms or by a group

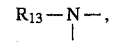

where $R_{13}$ is as defined above for $R_2$, $R_{11}$ is $C_2$–$C_3$alkylene and q is zero or 1, and, if n is 3, $X_3$ is a group of the formula (VIIIa) or (VIIIb) in which r is zero, $R_{15}$, $R_{18}$, $R_{21}$, $R_{22}$ and $R_{23}$, which can be identical or different are as defined above for $R_8$ and $R_{10}$, $R_{16}$ and $R_{17}$ which can be identical or different are $C_2$–$C_3$alkylene, u is zero or 1 and s and t which can be identical or different are integers from 3 to 5, and, if n is 4, $X_3$ is a group of the formula (IX) in which $R_{24}$ and $R_{28}$ which can be identical or different are as defined above for $R_8$ and $R_{10}$, and $R_{25}$, $R_{26}$ and $R_{27}$ which can be identical or different are $C_2$–$C_3$alkylene, with the proviso that at least one group of the formula (II) or of the formula (VII) is present in the compounds of the formula (I).

Those compounds of the formula (I) are of particular interest in which $X_1$ and $X_2$ which can be identical or different are a group of the formula (II), where $R_1$ is hydrogen or methyl, $R_2$ is $C_1$–$C_8$alkyl, cyclohexyl, 2,2,6,6-tetramethyl-4-piperidyl or 1,2,2,6,6-pentamethyl-4-piperidyl and A is —O—, or $X_1$ and $X_2$ are a group of the formula (Va) or (Vb), in which $R_5$ and $R_6$ which can be identical or different are as defined above for $R_2$, and $R_7$ is 2,2,6,6-tetramethyl-4-piperidyl or 1,2,2,6,6-pentamethyl-4-piperidyl and n is 1, 2, 3 or 4, and, if n is 1, $X_3$ is as defined above for $X_1$ and $X_2$, and, if n is 2, $X_3$ is a group

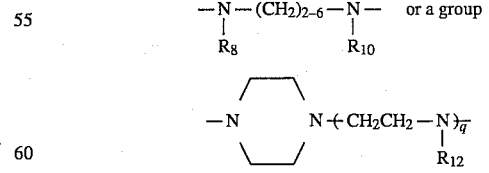

in which $R_8$, $R_{10}$ and $R_{12}$ which can be identical or different are as defined above for $R_2$ or are hydrogen, or $R_8$ and $R_{10}$ are also a group of the formula (VII), and q is zero or 1, and, if n is 3, $X_3$ is a group

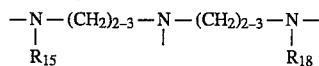

and, if n is 4, $X_3$ is a group

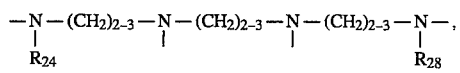

with $R_{15}$, $R_{18}$, $R_{24}$ and $R_{28}$ being as defined above for $R_8$ and $R_{10}$, with the proviso that at least one group of the formula (II) or the formula (VII) is present in the compounds of the formula (I).

The compounds of the present invention can be prepared by diverse processes known per se, like e.g. outlined in U.S. Pat. Nos. 4,108,829; 4,263,434; 4,883,860; 4,883,831 or 4,102,858.

According to process A, a dipiperidyl derivative of maleic or fumaric acid of the formula (X)

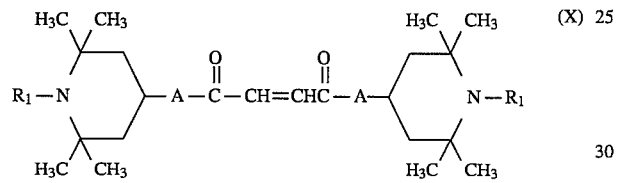

is added in a first stage to a suitable amine containing at least one $NH_2$ group, to obtain a compound containing one or more groups of the formula (XI)

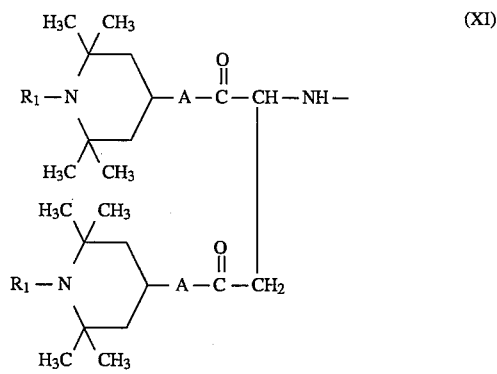

The reaction is carried out in an inert organic solvent, for example toluene, xylene, $C_1$–$C_5$alkanol, tetrahydrofuran, dioxane or dimethylformamide at a temperature from 0° to 150° C., preferably from 10° to 120° C.

In a subsequent stage, the dipiperidyl derivatives of aspartic acid thus obtained are reacted in any order and in the appropriate molar ratios with cyanuric chloride and other suitable reagents to obtain the compounds of the formula (I). The reaction is carried out in an inert organic solvent, for example toluene, xylene, trimethylbenzene, t-amyl alcohol or mixtures thereof, in any proportions of t-amyl alcohol with the abovementioned hydrocarbons, in the presence of a preferably inorganic base such as sodium or potassium hydroxide or carbonate at a temperature from –20° to 200° C., preferably from –10° to 180° C.

According to process B, compounds containing one or more groups of the formula

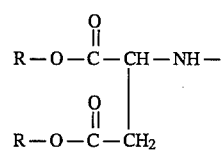

where R is $C_1$–$C_4$alkyl are first prepared by adding a di($C_1$–$C_4$alkyl) maleate or fumarate to a suitable amine containing at least one $NH_2$ group, by means of known procedures.

In a subsequent stage, the di($C_1$–$C_4$alkyl) aspartates thus obtained are reacted in any order and in the appropriate molar ratios with cyanuric chloride and other suitable reagents, following the procedure of process A, to obtain compounds containing one or more groups of the formula

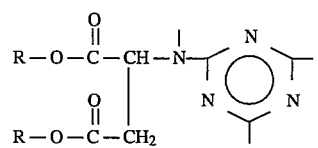

which are finally reacted with the appropriate molar quantity of a compound of the formula (XII)

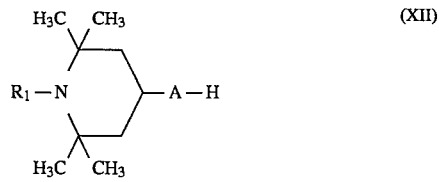

in the presence of a catalyst such as an alkali metal, a $C_1$–$C_4$alkoxide or amide or hydride of an alkali metal, a $C_1$–$C_4$alkoxide of Ti(IV) or dibutyltin oxide, the reaction being carried out in the absence of a solvent or in an inert organic solvent, for example toluene, xylene or trimethylbenzene at a temperature from 100° to 200° C., preferably from 110° to 180° C.

When working according to process B, if A is —O—, it is possible in the reaction with cyanuric chloride to use a compound of the formula (XII) in which A is —O— as temporary acceptor for the hydrochloric acid released, the resulting hydrochloride then being neutralized with a hydroxide or a $C_1$–$C_4$alkoxide of sodium or potassium to re-form the free base which thus becomes available for the transesterification reaction.

According to process C, the di($C_1$–$C_4$alkyl) aspartates prepared as shown under process B are reacted with the appropriate molar quantity of a compound of the formula (XII) as indicated in process B to obtain compounds containing one or more groups of the formula (XI), which are finally reacted in any order and in the appropriate molar ratios with cyanuric chloride and other reagents, following the procedure of process A, to obtain the compounds of the formula (I).

The various stages of the different reactions can be carried out in a single reactor or in the same solvent or in different solvents, without isolating the intermediates or after separating and, if desired, purifying them.

The compounds of the formulae (X) and (XII) can be prepared by known processes; the other reagents are commercially available or can be prepared according to the state of the art.

As mentioned at the outset, the compounds of the present invention are highly effective in improving the light stability, heat stability and oxidation stability of organic materials, in particular synthetic polymers and copolymers, and are particularly suitable for stabilizing polypropylene fibres.

Examples of organic materials which can be stabilized are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either $\pi$- or $\sigma$-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly($\alpha$-methylstyrene).

6. Copolymers of styrene or $\alpha$-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

The compounds of the formula (I) are particularly suitable for improving the light stability, heat stability and oxidation stability of polyolefins, especially polyethylene and polypropylene.

The invention also relates to compositions comprising an organic material that is susceptible to degradation induced by light, heat and/or oxidation and at least one compound of formula (I).

The compounds of the formula (I) can be used in mixtures with organic materials in various proportions depending on the nature of the material to be stabilized, on the end use and on the presence of other additives.

In general, it is appropriate to use, for example, 0.01 to 5% by weight of the compounds of the formula (I), relative to the weight of the material to be stabilized, preferably between 0.05 and 1%.

In general, the compounds of the formula (I) can be added to the polymeric materials before, during or after the polymerization or crosslinking of the said materials.

The compounds of the formula (I) can be incorporated in the polymeric materials in the pure form or encapsulated in waxes, oils or polymers.

The compounds of the formula (I) can be incorporated in the polymeric materials by various processes, such as dry mixing in the form of powder, or wet mixing in the form of solutions or suspensions or also in the form of a masterbatch; in such operations, the polymer can be used in the form of powder, granules, solutions, suspensions or in the form of latices.

The materials stabilized with the products of the formula (I) can be used for the production of mouldings, films, tapes, monofilaments, fibres, surface coatings and the like.

If desired, other conventional additives for synthetic polymers, such as antioxidants, UV absorbers, nickel stabilizers, pigments, fillers, plasticizers, antistatic agents, flameproofing agents, lubricants, corrosion inhibitors and metal deactivators, can be added to the mixtures of the compounds of the formula (I) with the organic materials.

Particular examples of additives which can be used in admixture with the compounds of the formula (I) are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)- 4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4 '-dimethyl- 6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl- 4-nonylphenol.

1.3. Hydroquinones and alkylated hydroquinones, for example 2,6-di-tert-butyl-4-methoxphenol, 2,5-di-tert-butylhydroquinone, 2,5-di-tert-amylhydroquinone, 2,6-di-phenyl- 4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl)adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dimethyl-4-hydroxyphenyl)disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[ 4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis [6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl- 5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl- 4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl- 4-hydroxy2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tris-(3,5-di-tert-butyl- 4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis-[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)- 2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis(octylmercapto)-6-(3,5-di-tert-butyl-4-hydroxyanilino)- 1,3,5-triazine, 2-octylmercapto-4,6-bis(3,5-di-tert-butyl-4-hydroxyanilino)- 1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)- 1,2,3-triazine, 1,3,5-tris-(3,5-di-tert-butyl-4-hydroxybenzyl)isocyanurate, 1,3,5-tris(4-tert-butyl-3-hydroxy- 2,6-dimethylbenzyl)isocyanurate, 2,4,6-tris(3,5-di-tert-butyl-4-hydroxyphenylphenylethyl)-1,3,5-triazine, 1,3,5-tris(3,5-di-tert-butyl-4-hydrophenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl- 4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono-or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl)propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

2. UV absorbers and light stabilisers 2.1.2-(2'-Hydroxyphenyl)benzotriazoles, for example 2-(2'-hydroxy-5 '-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl- 5'-tert-butyl-2'-hydroxyphenyl)enzotriazole, 2-(2'-hydroxy-4'-octyloxyphenyl)benzotriazole, 2-(3',5'-di-tert-amyl- 2'-hydroxyphenyl)benzotriazole, 2-(3',5'-bis-(α, α-dimethylbenzyl)-2'-hydroxyphenyl)benzotriazole, mixture of 2-(3'-tert-butyl-2'-hydroxy-5'-(2-octyloxycarbonylethyl)phenyl)- 5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-( 2-methoxycarbonylethyl)phenyl)-5-chloro-benzotriazole, 2-(3'-tert-butyl-2'-hydroxy-5'-(2-methoxycarbonylethyl)phenyl)bentriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO(CH$_2$)$_3$—]$_2$, where R=3'-tert-butyl-4'-hydroxy-5'-2H-benzotriazol-2-ylphenyl.

2.2.2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis(4-tert-butylbenzoyl)resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-piperidyl)sebacate, bis(2,2,6,6-tetramethyl-piperidyl)succinate, bis(1,2,2,6,6-pentamethylpiperidyl)sebacate, bis(1,2,2,6,6-pentamethylpiperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazasprio[4.5]decan-2,4-dion, bis(1-octyloxy-2,2,6,6-tetramethylpiperidyl)sebacate, bis(1-octyloxy-2,2,6,6-tetramethylpiperidyl)succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2, 5-dione, 3-dodecyl-1-(1,2,2,6,6-pentamethyl-4-piperidyl)pyrrolidine-2,5-dione.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and para-methoxy-disubstituted oxanilides and mixtures of o- and p-ethoxy-disubstituted oxanilides.

2.8.2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphsophite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl)methylphosphite, bis(2,4-di-tert-butyl-6-methylphenyl)ethylphosphite.

5. Hydroxylamines, for example dibenzylhydroxylamine, dioctylhydroxylamine, didodecylhydroxylamine, ditetradecylhydroxylamine, dihexadecylhydroxylamine, dioctadecylhydroxylamine, 1-hydroxy-2,2,6,6-tetramethyl-4-piperidyl benzoate or bis(1-hydroxy-2,2,6,6-tetramethyl-4-piperidyl)sebacate.

6. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

7. Polyamide stabilisers, for example, copper salts in combination with iodides and/or phosphorus compounds and salts of divalent manganese.

8. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

9. Nucleating agents, for example, 4-tert-butylbenzoic acid, adipic acid, diphenylacetic acid.

10. Fillers and reinforcing agents, for example, calcium carbonate, silicates, glass fibres, asbestos, talc, kaolin, mica, barium sulfate, metal oxides and hydroxides, carbon black, graphite.

11. Other additives, for example, plasticisers, lubricants, emulsifiers, pigments, optical brighteners, flameproofing agents, antistatic agents and blowing agents.

12. Benzofuranones and indolinones, for example those disclosed in U.S. Pat. Nos. 4,325,863, 4,338,244, 5,175,312, 5,216,052, 5,252,643, DE-A-4 316 611, DE-A-4 316 622, DE-A-4 316 876, EP-A-0 589 839 or EP-A-0 591 102 or 3-[4-( 2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one.

The compounds of the formula (I) can also be used as stabilizers, especially as light stabilizers, for almost all materials known in the art of photographic reproduction and other reproduction techniques as e.g. described in Research Disclosure 1990, 31429 (pages 474 to 480).

Several examples of the preparation and use of the compounds of the formula (I) are reported for more detailed illustration of the present invention; these examples are given solely for illustrative purposes and do not imply any restriction.

EXAMPLE 1 a) Preparation of tetrakis(2,2,6,6-tetramethyl-4-piperidyl) N,N'-hexamethylenediaspartate.

63.1 g (0.16 mol) of bis(2,2,6,6-tetramethyl-4-piperidyl)maleate and 9.3 g (0.08 mol) of hexamethylenediamine in 120 ml of dimethylformamide are heated for 16 hours at 90° C. and then allowed to cool slowly to ambient temperature. The precipitate which has formed is separated off by filtration, washed with a little dimethylformamide and then with acetone and finally dried in vacuo. The product obtained melts at 124°–126° C.

Analysis for $C_{50}H_{92}N_6O_8$ calculated: C=66.34%; H=10.24%; N=9.28% found: C=66.17%; H=10.24%; N=9.30% b) Preparation of the product of the formula

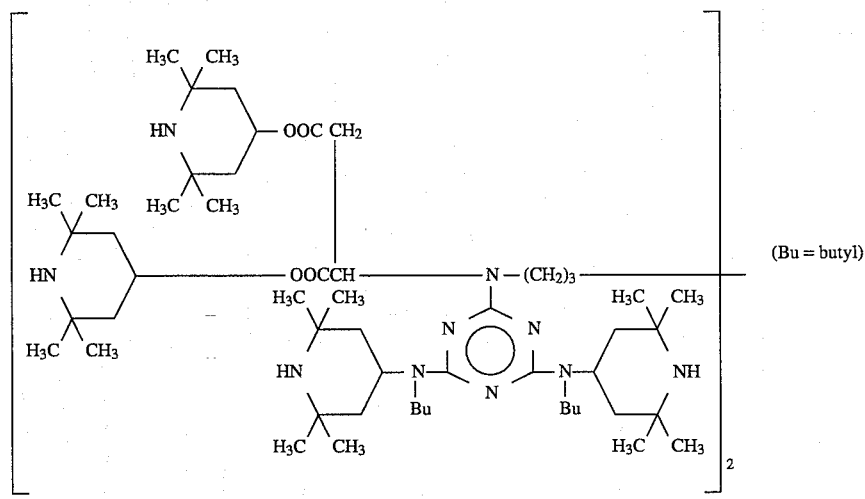

31.7 g (0.035 mol) of tetrakis(2,2,6,6-tetramethyl-4-piperidyl) N,N'-hexamethylenediaspanate are added in the course of 45 minutes to a solution of 12.9 g (0.07 mol) of cyanuric chloride in 130 ml of dichloromethane, maintaining the temperature at −10° C. After the end of the addition, the mixture is stirred for 30 minutes at −10° C., and the temperature is then allowed to rise up to 0° C. and, at this temperature, a solution of 2.8 g (0.07 mol) of NaOH in 15 ml of water is added slowly, the mixture is stirred for 30 minutes at 20° C. and the aqueous phase is separated off.

150 ml of mesitylene and 41.6 g (0.196 mol) of 4-butylamino-2,2,6,6-tetramethylpiperidine are added, the dichloromethane is distilled off and the mixture is heated for 3 hours at 140° C.

38.7 g (0.28 mol) of ground $K_2CO_3$ are added and the mixture is heated under reflux for 12 hours, the water of reaction being separated off azeotropically.

After cooling to ambient temperature, the reaction mixture is filtered in order to separate off the inorganic salts, and the solvent and the excess of 4-butylamino-2,2,6,6-tetramethylpiperidine are removed in vacuo.

The product obtained melts at 96°–99° C. Analysis for $C_{108}H_{198}N_{20}O_8$ calculated: C=68.10%; H=10.48%; N=14.71% found: C=67.89%; H=10.40%; N=14.56%

EXAMPLE 2

Preparation of the product of the formula

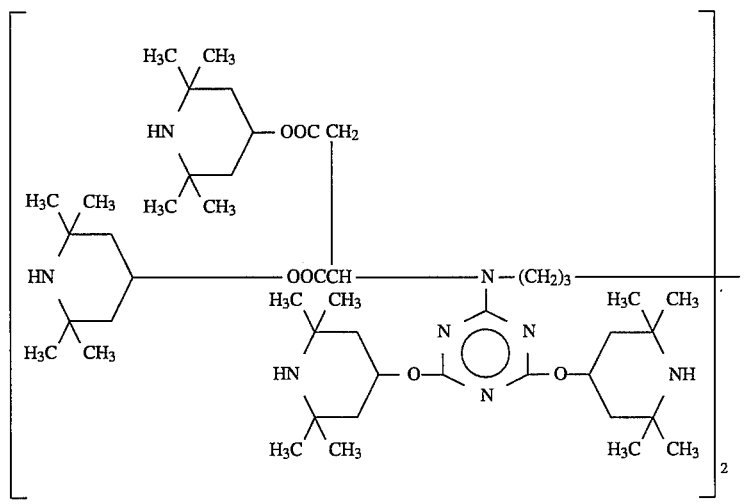

21.7 g (0.024 mol) of tetrakis(2,2,6,6-tetramethyl-4-piperidyl) N,N'-hexamethylenediaspartate and 20.5 g (0.048 mol) of 2-chloro-4,6-bis(2,2,6,6-tetramethyl-4-piperidyloxy)-1,3,5-triazine in 100 ml of t-amyl alcohol are heated under reflux for 12 hours. 13.3 g (0.096 mol) of ground $K_2CO_3$ are added and the mixture is heated under reflux for 8 hours.

The solvent is evaporated in vacuo and the residue is taken up in 150 ml of dichloromethane and 50 ml of water. The aqueous phase is separated off and the organic phase is washed with water, dried over anhydrous $Na_2SO_4$ and evaporated in vacuo.

The product obtained melts at 95°–98° C. Analysis for $C_{92}H_{162}N_{16}O_{12}$ calculated: C=65.60%; H=9.69%; N=13.30% found: C=65.16%; H=9.69%; N=13.25%

EXAMPLE 3 a) The tetrakis(1,2,2,6,6-pentamethyl-4-piperidyl) N,N'-hexamethylenediaspartate is prepared as described in Example 1a by reacting 42.3 g (0.1 mol) of bis(1,2,2,6,6-pentamethyl-4-piperidyl)maleate with 5.8 g (0.05 mol) of hexamethylenediamine.

The product obtained is a dense oil. Analysis for $C_{54}H_{100}N_6O_8$ calculated: C=67.46%; H=10.48%; N=8.74% found: C=67.44%; H=10.47%; N=8.67% b) The product of the formula

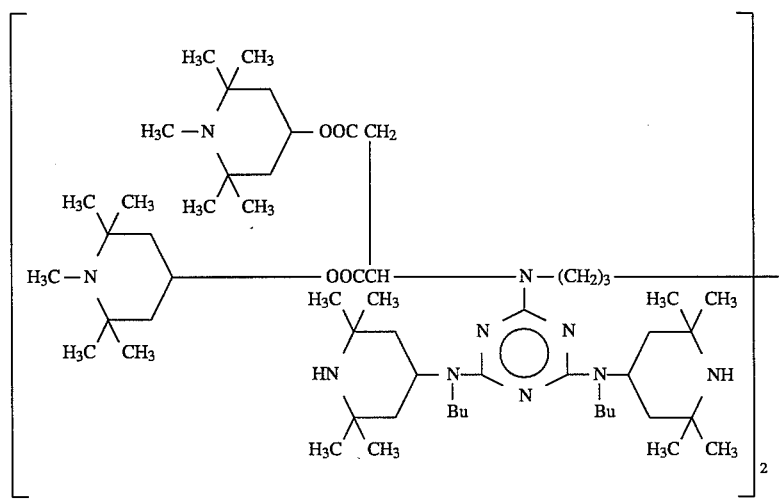

is prepared as described in Example 1b by reacting 38.5 g (0.04 mol) of tetrakis(1,2,2,6,6-pentamethyl-4-piperidyl) N,N'-hexamethylenediaspartate with 14.8 g (0.08 mol) of cyanuric chloride and 47.6 g (0.224 mol) of 4-butylamino-2,2,6,6-tetramethylpiperdine.

The product obtained melts at 93°–95° C. Analysis for $C_{112}H_{206}N_{20}O_8$ calculated: C=68.60%; H=10.59%; N=14.28% found: C=68.60%; H=10.55%; N=14.21%

EXAMPLE 4

The product of the formula

EXAMPLE 5 a) The tetrakis(2,2,6,6-tetramethyl-4-piperidyl) N,N'-(iminodiethylene)diaspartate is prepared as described in Example 1a by reacting 94.7 g (0.24 mol) of bis(2,2,6,6-tetramethyl-4-piperidyl)maleate with 12.4 g (0.12 mol) of diethylenetriamine.

The product obtained is a dense oil. Analysis for $C_{48}H_{89}N_7O_8$ calculated: C=64.61%; H=10.05%; N=10.99% found: C=64.02%; H=9.90%; N=10.91% b) The product of the formula

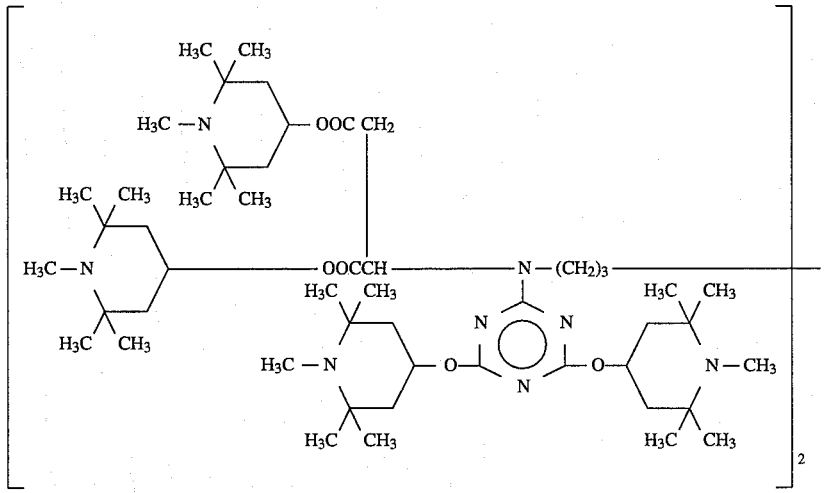

is prepared as described in Example 2 by reacting 19.2 g (0.02 mol) of tetrakis(1,2,2,6,6-pentamethyl-4-piperidyl) N,N'-hexamethylenediaspartate with 18.2 g (0.04 mol) of 2-chloro-4,6-bis(1,2,2,6,6-pentamethyl-4-piperidyloxy)-1,3,5-triazine.

The product obtained melts at 109°–112° C. Analysis for $C_{100}H_{178}N_{16}O_{12}$ calculated: C=66.85%; H=9.99%; N=12.47% found: C=66.76%; H=9.93%; N=12.43%

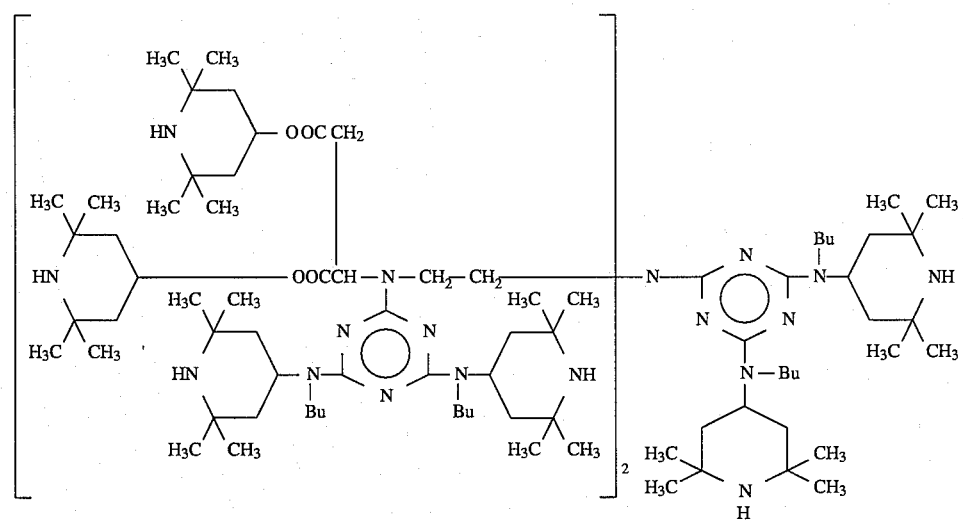

is prepared as described in Example 1b by reacting 26.8 g (0.03 mol) of tetrakis(2,2,6,6-tetramethyl-4-piperidyl) N,N'-(iminodiethylene)diaspartate with 16.6 g (0.09 mol) of cyanuric chloride and 53.5 g (0.252 mol) of 4-butylamino-2,2,6,6-tetramethylpiperidine.

The product obtained melts at 111°–113° C. Analysis for $C_{135}H_{248}N_{28}O_8$ calculated: C=67.80%; H=10.45%; N=16.40% found: C=66.90%; H=10.41%; N=16.30%

EXAMPLE 6 a) The tetrakis(1,2,2,6,6-pentamethyl-4-piperidyl) N,N'-[iminobis(trimethylene)]diaspartate is prepared as described in Example 1a by reacting 67.6 g (0.16 mol) of bis(1,2,2,6,6-pentamethyl-4-piperdiyl)maleate with 10.5 g (0.08 mol) of bis(3-aminopropyl)amine.

The product obtained is a dense oil. Analysis for $C_{54}H_{101}N_7O_8$ calculated: C=66.42%; H=10.43%; N=10.04% found: C=65.89%; H=10.40%; N=9.98% b) The product of the formula

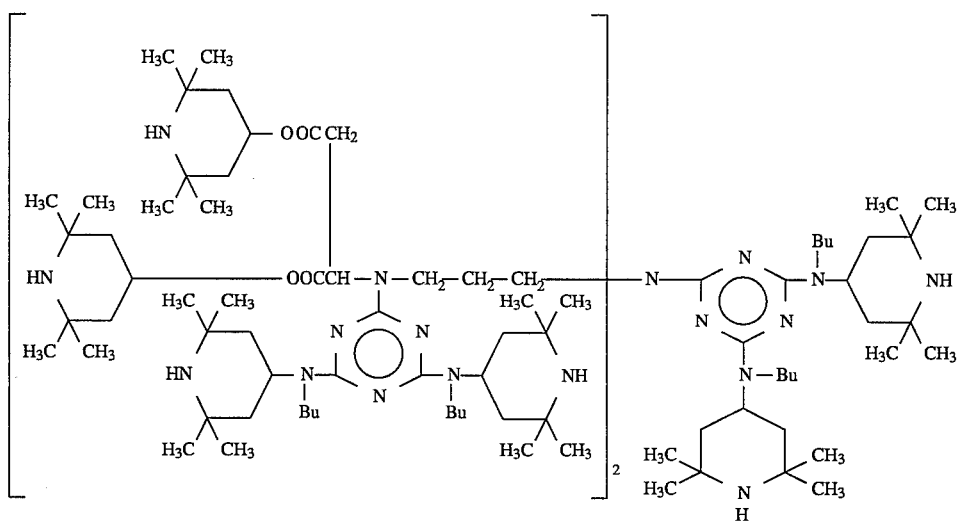

is prepared as described in Example 1b by reacting 39.1 g (0.04 mol) of tetrakis(1,2,2,6,6-pentamethyl-4-piperidyl) N,N'-[iminobis(trimethylene)]diaspartate with 22.1 g (0.12 mol) of cyanuric chloride and 71.4 g (0.336 mol) of 4-butylamino-2,2,6,6-tetramethylpiperidine.

The product obtained melts at 118°–121° C. Analysis for $C_{141}H_{260}N_{28}O_8$ calculated: C=68.40%; H=10.58%; N=15.84% found: C=68.49%; H=10.46%; N=15.71%

EXAMPLE 7

Preparation of the product of the formula

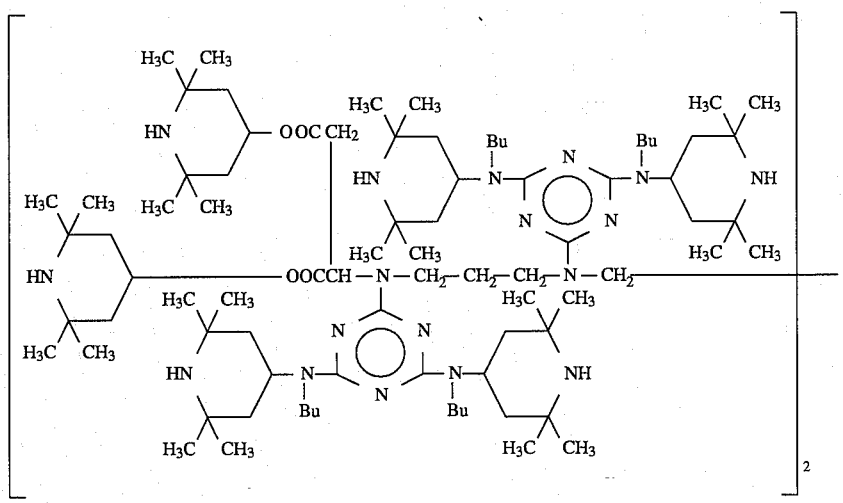

23.1 g (0.05 mol) of tetramethyl N,N'-[ethylenebis(iminotrimethylene)]diaspartate are added in the course of 45 minutes to a mixture, maintained at −10° C., of 36.9 g (0.2 mol) of cyanuric chloride and 46.2 g (0.27 mol) of 2,2,6,6-tetramethyl-4-piperidinol in 500 ml of xylene. After the end of the addition, the mixture is stirred for 30 minutes at −10° C. and for 2 hours at 20° C.

85 g (0.4 mol) of 4-butylamino-2,2,6,6-tetramethylpiperidine are added and the mixture is heated for 3 hours at 90° C. 55.3 g (0.4 mol) of ground $K_2CO_3$ are added and the mixture is heated under reflux for 12 hours.

After cooling to 20° C., 11.9 g (0.22 mol) of sodium methoxide are added and the mixture is stirred for 15 minutes and then heated under reflux for 12 hours, with the methanol released being separated off by distillation.

After cooling to ambient temperature, the reaction mixture is washed with water up to complete removal of chlorine ions and is finally dried by heating to 200° C. at 6 mbar, in order to separate off the excess 2,2,6,6-tetramethyl-4-piperidinol.

The product obtained melts at 126°–129° C. Analysis for $C_{168}H_{310}N_{36}O_8$ calculated: C=68.11%; H=10.55%; N=17.02% found: C=67.90%; H=10.42%; N=17.00%

EXAMPLE 8 a) Preparation of diethyl N-(2,2,6,6-tetramethyl-4-piperidyl)aspartate.

78.1 g (0.5 mol) of 4-amino-2,2,6,6-tetramethylpiperidine and 86.1 g (0.5 mol) of diethyl maleate in 200 ml of tetrahydrofuran are heated under reflux for 6 hours. The solvent is evaporated in vacuo and the product is separated off by distillation: boiling point 116°–118° C./0.5 mbar.

Analysis for $C_{17}H_{32}N_2O_4$ calculated: C=62.17%; H=9.82%; N=8.53% found: C=62.01%; H=9.78%; N=8.49% b) Preparation of the product of the formula

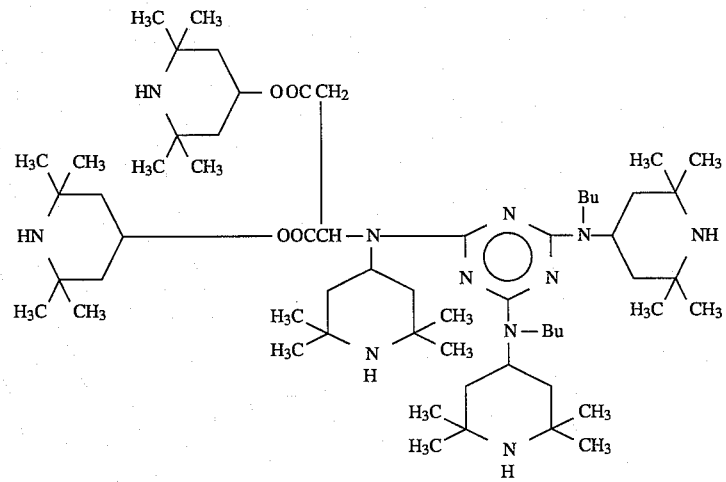

A solution of 32.8 g (0.1 mol) of diethyl N-(2,2,6,6-tetramethyl-4-piperidyl)aspartate in 100 ml of xylene is added slowly to a solution of 18.4 g (0.1 mol) of cyanuric chloride in 100 ml of xylene, maintaining the temperature at 0° C. The mixture is stirred for 3 hours at ambient temperature, a solution of 13.8 g (0.1 mol) of $K_2CO_3$ in 50 ml of water is then added slowly, maintaining the temperature at 10° C., the mixture is stirred for 1 hour at ambient temperature and the aqueous phase is separated off.

42.5 g (0.2 mol) of 4-butylamino-2,2,6,6-tetramethylpiperdine are added and the mixture is heated under reflux for 3 hours, the water being separated off azeotropically.

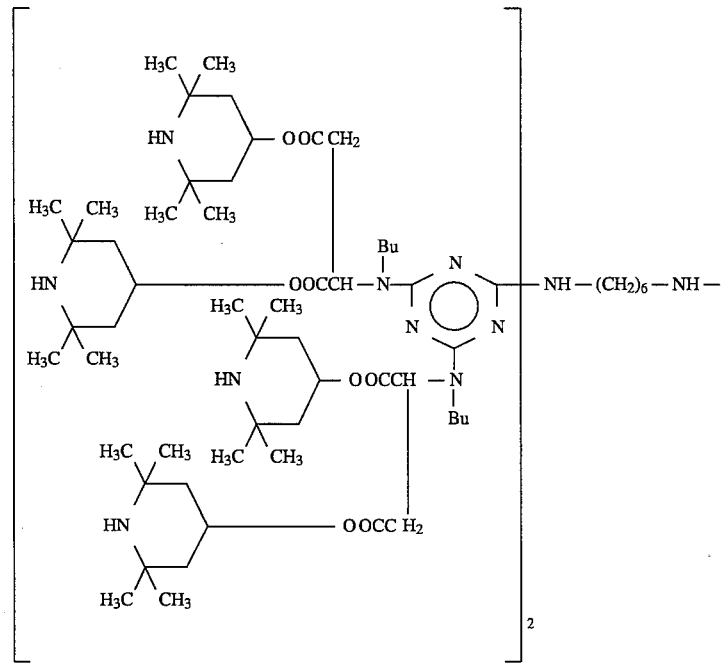

The mixture is cooled to 60° C., 41.5 g (0.3 mol) of ground $K_2CO_3$ are added, and the mixture is again heated under reflux for 8 hours, with azeotropic removal of the water of reaction. The mixture is then cooled to 50° C. and filtered in order to separate off the inorganic salts.

37.7 g (0.24 mol) of 2,2,6,6-tetramethyl-4-piperidinol and 0.8 ml of Ti(IV) isopropoxide are added to the solution thus obtained and the mixture is heated under reflux for 8 hours, removing the ethanol formed during the reaction. After cooling to ambient temperature, the solution is washed several times with water in order to remove the excess 2,2,6,6-tetramethyl-4-piperidinol and evaporated in vacuo. The oily residue obtained crystallizes slowly from hexane: melting point 79°–81° C.

Analysis for $C_{60}H_{111}N_{11}O_4$ calculated: C=68.59%; H=10.65%; N=14.66% found: C=68.19%; H=10.58%; N=14.66%

EXAMPLE 9 a) Preparation of bis(2,2,6,6-tetramethyl-4-piperidyl) N-butylaspartate.

43.5 g (0.2 mol) of dimethyl N-butylaspartate, 78.6 g (0.5 mol) of 2,2,6,6-tetramethyl-4-piperidinol and 0.5 ml of Ti(IV) isopropoxide in 200 ml of xylene are heated under reflux for 10 hours with removal of the methanol formed during the reaction.

After cooling to ambient temperature, the mixture is washed several times with water in order to remove the excess 2,2,6,6-tetramethyl-4-piperidinol and evaporated by heating up to 100° C. at 2 mbar.

The product is obtained as a oily residue. Analysis for $C_{26}H_{49}N_3O_4$ calculated: C=66.77%; H=10.56%; N=8.98% found: C=66.63%; H=10.52%; N=8.94% b) Preparation of the product of the formula

A solution of 56.1 g (0.12 mol) of bis(2,2,6,6-tetramethyl-4-piperidyl) N-butylaspartate in 50 ml of xylene is added slowly to a solution of 22.1 g (0.12 mol) of cyanuric chloride in 250 ml of xylene, maintaining the temperature at 20° C. After the end of the addition, the mixture is stirred for 1 hour at 20° C., 20 g (0.145 mol) of ground $K_2CO_3$ are added and the mixture is stirred for a further 2 hours at 20° C.

After heating to 80° C., a solution of 56.1 g (0.12 mol) of bis(2,2,6,6-tetramethyl-4-piperidyl) N-butylaspartate in 50 ml of xylene is added slowly.

The mixture is heated for 2 hours at 110° C., 20 g (0.145 mol) of ground $K_2CO_3$ are added and the mixture is heated again at 110° C. for 5 hours.

After cooling to 80° C., 7 g (0.06 mol) of hexamethylenediamine and 29 g (0.21 mol) of ground $K_2CO_3$ are added and the mixture is heated under reflux for 8 hours with the water of reaction being distilled off azeotropically.

After cooling to ambient temperature, the mixture is filtered in order to separate off the inorganic salts, and the solvent is evaporated in vacuo.

The product obtained melts at 77°–80° C. Analysis for $C_{116}H_{206}N_{20}O_{16}$ calculated: C=65.20%; H=9.72%; N=13.11% found: C=64.50%; H=9.61%; N=12.96%

EXAMPLE 10

Preparation of the product of the formula

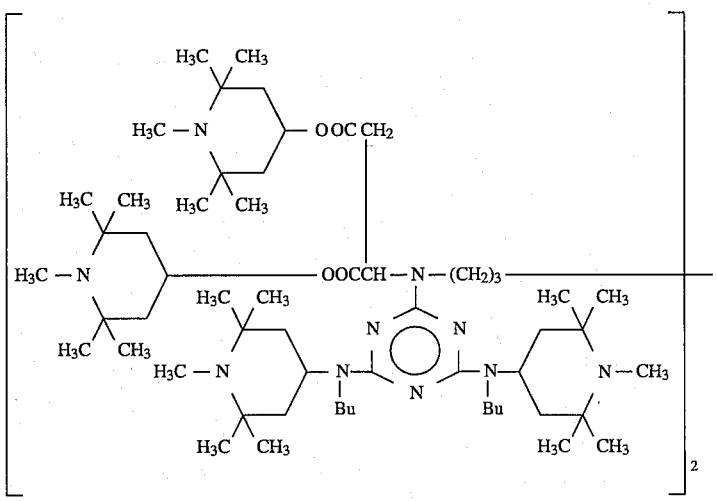

A solution containing 4.3 g (0.144 mol) of formaldehyde (free of methanol) and 6.6 g (0.144 mol) of formic acid in 50 ml of water is added in the course of 2 hours to a solution, heated under reflux, of 28.6 g (0.015 mol) of the product from Example 1 in 150 ml of toluene, with simultaneous azeotropic removal of the water added and of the water of reaction.

After cooling to ambient temperature, a solution of 5.8 g of NaOH in 50 ml of water is added, the mixture is stirred for 15 minutes and the aqueous phase is separated off.

The organic phase is washed with water and evaporated in vacuo.

The product obtained melts at 119°–121° C. Analysis for $C_{116}H_{214}N_{20}O_8$ calculated: C=69.07%; H=10.69%; N=13.89% found: C=68.56%; H=10.53%; N=13.69%

EXAMPLE 11

The product of the formula (0.01 mol) of the product from Example 6 with 3.6 g (0.12 mol) of formaldehyde and 5.5 g (0.12 mol) of formic acid.

The product obtained melts at 133°–135° C. Analysis for $C_{147}H_{272}N_{28}O_8$ calculated: C=68.97%; H=10.71%; N=15.32% found: C=68.41%; H=10.54%; N=15.30%

EXAMPLE 12

The product of the formula

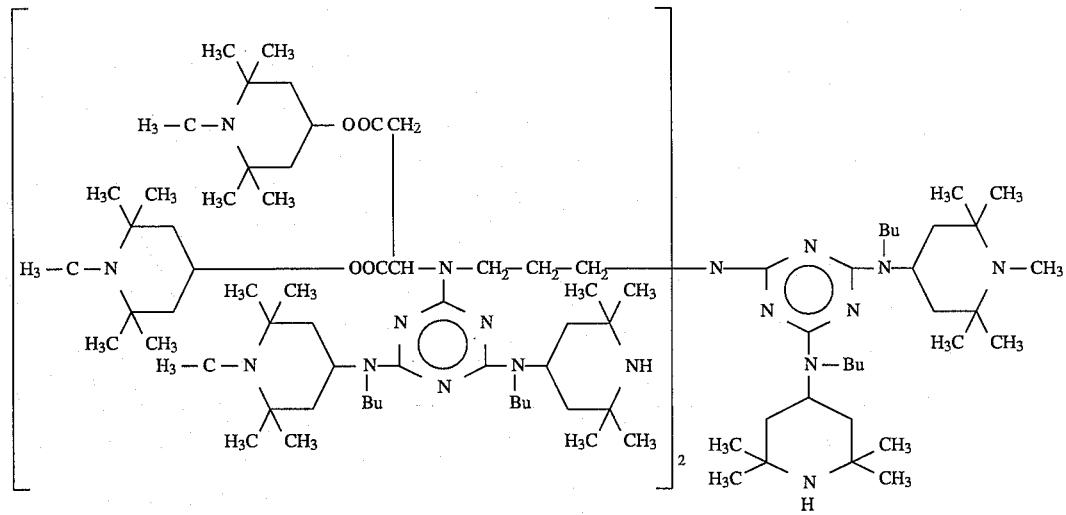

is prepared as described in Example 10 by reacting 24.8 g

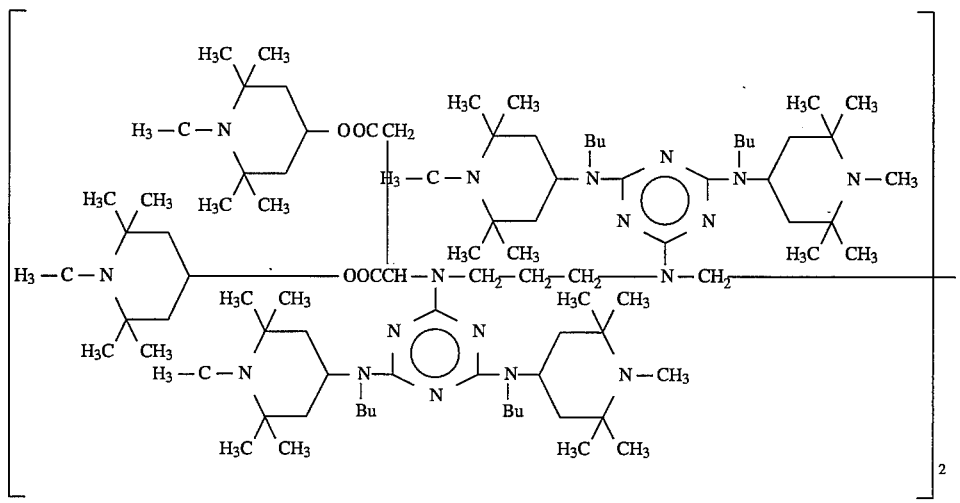

is prepared as described in Example 10 by reacting 29.6 g (0.01 mol) of the product from Example 7 with 4.3 g (0.144 mol) of formaldehyde and 6.6 g (0.144 mol) of formic acid.

The product obtained melts at 141°–144° C. Analysis for $C_{180}H_{334}N_{36}O_8$ calculated: C=69.05%; H=10.75%; N=16.11% found: C=68.81%; H=10.58%; N=15.99%

EXAMPLE 13

(Light-stabilizing action in polypropylene fibres)

2.5 g of each of the products indicated in Table 1, 1 g of tris(2,4-di-t-butylphenyl)phosphite, 0.5 g of calcium monoethyl 3,5-di-t-butyl-4-hydroxybenzylphosphonate, 1 g of calcium stearate and 2.5 g of titanium dioxide are mixed in a turbo mixer with 1000 g of a polypropylene powder of melt index=12 g/10 minutes (measured 230° C. and 2.16 kg).

The mixtures are extruded at 230°–245° C. to give polymer granules which are then converted into fibres, using a pilot-type apparatus (Leonard-Sumirago (VA) Italy) operating under the following conditions:

extruder temperature: 230°–245° C.

head temperature: 255°–260° C.

stretch ratio: 1:3.5 count: 11 dtex per filament

The fibres thus prepared are exposed, mounted on a white card, in a model 65 WR Weather-O-Meter (ASTM D2565-85) with a black panel temperature of 63° C.

The residual tenacity is measured on samples taken after various times of exposure to light by means of a constant-speed tensometer, and the exposure time in hours ($T_{50}$) needed to halve the initial tenacity is then calculated.

The fibres prepared under the same conditions as indicated above, but without addition of the stabilizers according to the invention, are exposed for comparison. The results obtained are shown in Table 1. The longer the time the better is the stabilizing effect.

TABLE 1

| Stabilizer | $T_{50}$(hours) |
| --- | --- |
| None | 260 |
| Product from Example 1 | 2900 |

TABLE 1-continued

| Stabilizer | $T_{50}$(hours) |
| --- | --- |
| Product from Example 3 | 2630 |
| Product from Example 4 | 2900 |
| Product from Example 5 | 2600 |
| Product from Example 6 | 2600 |
| Product from Example 11 | 2600 |

EXAMPLE 14

(Light-stabilizing action in polypropylene tapes)

1 g of each of the compounds indicated in Table 2, 1 g of tris(2,4-di-tert-butylphenyl)phosphite, 0.5 g of pentaerythritol tetrakis[3-(3,5-di-tert-butyl-4-hydroxy-phenyl)propionate] and 1 g of calcium stearate are mixed in a turbo mixer with 1000 g of polypropylene powder having a melt index=2 g/10 min. (measured at 230° C. and 2.16 kg). The mixtures are extruded at 200°–220° C. to give polymer granules which are subsequently converted to streched tapes of 50 μm thickness and 2.5 mm width, using a semi-industrial type of apparatus (Leonard-Sumirago (VA), Italy) and working under the following conditions:

extruder temperature: 210°–230° C.

head temperature: 240°–260° C.

stretch ratio: 1:6

The tapes thus prepared are mounted on white card and exposed in a Weather-O-Meter 65 WR (ASTM D 2565-85) with a black panel temperature of 63° C. The residual tenacity is measured, by means of a constant velocity tensometer, on samples taken after various light exposure times; from this, the exposure time (in hours) required to halve the initial tenacity ($T_{50}$) is measured. By way of comparison, tapes prepared under the same conditions as indicated above, but without the addition of the stabilizers of the present invention, are exposed. The results obtained are shown in Table 2. The longer the time the better is the stabilizing effect.

TABLE 2

| Stabilizer | $T_{50}$(hours) |
|---|---|
| None | 530 |
| Product from Example 2 | 3590 |

What is claimed is:

1. A compound of the formula (I)

$$\left( X_1 - \underset{X_2}{\underset{|}{N}} \underset{N}{\overset{N}{\bigwedge}} N - \right)_n X_3 \tag{I}$$

in which $X_1$ and $X_2$ which can be identical or different are a group of the formula (II)

(II) [structure showing two piperidine-containing groups with $R_1$—N—, $H_3C$, $CH_3$ substituents, —A—C(=O)—CH(—N—$R_2$)— and —A—C(=O)—CH$_2$ groups]

in which $R_1$ is hydrogen, $C_1$–$C_8$alkyl, O, OH, $CH_2CN$, $C_1$–$C_{18}$alkoxy, $C_5$–$C_{12}$ cycloalkoxy, $C_3$–$C_6$alkenyl, $C_7$–$C_9$phenylalkyl unsubstituted or mono-, di- or tri-substituted on the phenyl by $C_1$–$C_4$alkyl; or aliphatic $C_1$–$C_8$acyl, $R_2$ is hydrogen, $C_1$–$C_{18}$alkyl, $C_5$–$C_{12}$cycloalkyl unsubstituted or mono-, di- or tri-substituted by $C_1$–$C_4$alkyl; $C_7$–$C_9$phenylalkyl unsubstituted or mono-, di- or tri-substituted on the phenyl by $C_1$–$C_4$alkyl; tetrahydrofurfuryl or a group of the formula (III)

(III) [2,2,6,6-tetramethylpiperidin-4-yl structure with $R_3$—N—]

where $R_3$ is as defined for $R_1$ or $C_2$–$C_4$alkyl substituted in the 2-, 3- or 4-position by $C_1$–$C_8$alkoxy, by di($C_1$–$C_4$alkyl)amino or by a group of the formula (IV)

$$Q_1 \diagdown N— \tag{IV}$$

where $Q_1$ is a direct bond, —O—, —$CH_2$—, —$CH_2CH_2$— or $$CH_3—N—,$$

and A is —O— or $$R_4—N—$$

with $R_4$ being hydrogen or $C_1$–$C_{12}$alkyl, or $X_1$ and $X_2$ are a group of the formula (IV) or one of the groups of the formulae (Va)–(Ve)

$$R_5—N— \atop R_6 \tag{Va}$$

$$R_7—O— \tag{Vb}$$

(Vc) [structure]

(Vd) [structure]

(Ve) [structure]

in which $R_3$ is as defined above, $R_5$, $R_6$ and $R_7$ which can be identical or different are as defined for $R_2$, or $R_7$ is also $C_3$–$C_{18}$alkenyl or phenyl unsubstituted or mono-, di- or tri-substituted by $C_1$–$C_4$alkyl or $C_1$–$C_4$alkoxy;

$Q_2$ is —CO—, —$CH_2CH_2$—, —COCO—, —$CH_2CO$— or —$COCH_2CO$— and p is zero or 1, n is 1, 2, 3 or 4 and, if n is 1, $X_3$ is as defined for $X_1$ and $X_2$, and, if n is 2, $X_3$ is one of the groups of the formulae (VIa)–(VIc)

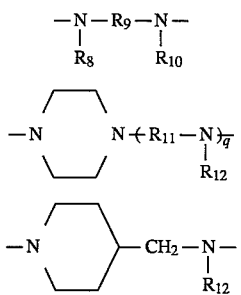
(VIa)

(VIb)

(VIc)

in which

R$_8$, R$_{10}$ and R$_{12}$ which can be identical or different are as defined for R$_2$, or R$_8$ and R$_{10}$ are also a group of the formula (VII)

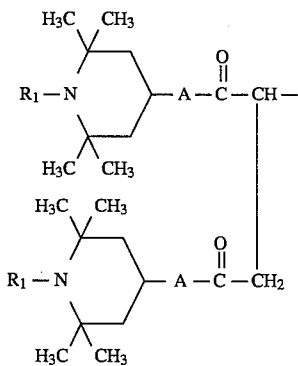
(VII)

with R$_1$ and A as defined above, R$_9$ is C$_2$–C$_{12}$alkylene, C$_5$–C$_7$cycloalkylene, C$_5$–C$_7$cycloalkylenedi(C$_1$–C$_4$alkylene), C$_1$–C$_4$alkylenedi(C$_5$–C$_7$cycloalkylene), phenylenedi(C$_1$–C$_4$alkylene) or C$_4$–C$_{12}$alkylene interrupted by a 1,4-piperazinediyl group or by 1, 2 or 3 oxygen atoms or by 1 or 2

groups, where R$_{13}$ is as defined for R$_2$ or is aliphatic C$_1$–C$_{12}$acyl or (C$_1$–C$_{12}$alkoxy)carbonyl, or R$_9$ is also a group

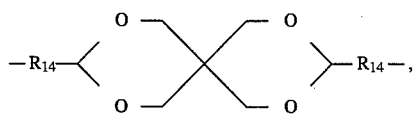

R$_{11}$ and R$_{14}$ are C$_2$–C$_6$alkylene and q is zero or 1, and if n is 3, X$_3$ is a group of the formula (VIIIa) or (VIIIb)

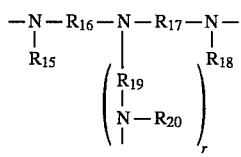
(VIIIa)

-continued

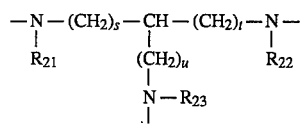
(VIIIb)

in which

R$_{15}$, R$_{18}$, R$_{20}$, R$_{21}$, R$_{22}$ and R$_{23}$ which can be identical or different are as defined above for R$_8$ and R$_{10}$, R$_{16}$, R$_{17}$ and R$_{19}$ which can be identical or different are C$_2$–C$_6$alkylene, r and u are zero or 1, and s and t which can be identical or different are integers from 2 to 6, and, if n is 4, X$_3$ is a group of the formula (IX)

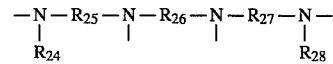
(IX)

in which

R$_{24}$ and R$_{28}$ which can be identical or different are as defined above for R$_8$ and R$_{10}$, and R$_{25}$, R$_{26}$ and R$_{27}$ which can be identical or different are C$_2$–C$_6$alkylene, with the proviso that at least one group of the formula (II) or of the formula (VII) is present in the compounds of the formula (I).

2. A compound of the formula (I) according to claim 1, in which R$_1$ and R$_3$ are hydrogen, C$_1$–C$_4$alkyl, OH, C$_6$–C$_{12}$alkoxy, C$_5$–C$_8$cycloalkoxy, allyl, benzyl or acetyl.

3. A compound of the formula (I) according to claim 1, in which X$_1$ and X$_2$ which can be identical or different are a group of the formula (II) in which R$_2$ is hydrogen, C$_1$–C$_{16}$alkyl, C$_5$–C$_8$cycloalkyl unsubstituted or mono-, di- or tri-substituted by C$_1$–C$_4$alkyl; benzyl unsubstituted or mono-, di- or tri-substituted on the phenyl by C$_1$–C$_4$alkyl; tetrahydrofurfuryl, a group of the formula (III), C$_2$–C$_3$alkyl substituted in the 2- or 3-position by C$_1$–C$_4$-alkoxy, by di-(C$_1$–C$_4$alkyl)amino or by a group of the formula (IV), where Q$_1$ is a direct bond, —O—, —CH$_2$— or —CH$_2$CH$_2$—, and A is —O— or

R$_4$—N—, with R$_4$ being hydrogen or C$_1$–C$_{10}$alkyl, or X$_1$ and X$_2$ are a group of the formula (IV) or one of the groups of the formulae (Va)–(Ve), in which R$_5$, R$_6$ and R$_7$ which can be identical or different are as defined for R$_2$, or R$_7$ is also C$_3$–C$_{12}$alkenyl or phenyl unsubstituted or mono-, di- or tri-substituted by C$_1$–C$_4$alkyl or C$_1$–C$_4$alkoxy, Q$_2$ is —CO—, —CH$_2$CH$_2$—, —COCO— or —COCH$_2$CO—, p is zero or 1 and n is 1, 2, 3 or 4, and, if n is 1, X$_3$ is as defined for X$_1$ and X$_2$, and, if n is 2, X$_3$ is one of the groups of the formulae (VIa)–(VIc) in which R$_8$, R$_{10}$ and R$_{12}$ which can be identical or different are as defined above for R$_2$ or R$_8$ and R$_{10}$ are also a group of the formula (VII), R$_9$ is C$_2$–C$_{10}$alkylene, cyclohexylene, cyclohexylenedimethylene, methylenedicyclohexylene, phenylenedimethylene, C$_4$–C$_{10}$alkylene interrupted by a 1,4-piperazinediyl group or by 1, 2 or 3 oxygen atoms or by 1 or 2

groups, where $R_{13}$ is as defined above for $R_2$ or is aliphatic $C_1$–$C_8$acyl or ($C_1$–$C_8$alkoxy)carbonyl, or $R_9$ is also a group

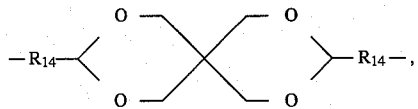

$R_{11}$ and $R_{14}$ are $C_2$–$C_4$alkylene and q is zero or 1, and, if n is 3, $X_3$ is a group of the formula (VIIIa) or (VIIIb), in which $R_{15}$, $R_{18}$, $R_{20}$, $R_{21}$, $R_{22}$ and $R_{23}$ which can be identical or different are as defined above for $R_8$ and $R_{10}$, $R_{16}$, $R_{17}$ and $R_{19}$ which can be identical or different are $C_2$–$C_4$alkylene, r and u are zero or 1 and s and t which can be identical or different are integers from 3 to 6 and, if n is 4, $X_3$ is a group of the formula (IX) in which $R_{24}$ and $R_{28}$ which can be identical or different are as defined above for $R_8$ and $R_{10}$, and $R_{25}$, $R_{26}$ and $R_{27}$ which can be identical or different are $C_2$–$C_4$alkylene, with the proviso that at least one group of the formula (II) or of the formula (VII) is present in the compounds of the formula (I).

4. A compound of the formula (I) according to claim 1, in which $X_1$ and $X_2$ which can be identical or different are a group of the formula (II), where $R_2$ is hydrogen, $C_1$–$C_{14}$alkyl, cyclohexyl unsubstituted or mono-, di- or tri-substituted by $C_1$–$C_4$alkyl; benzyl, tetrahydrofurfuryl, a group of the formula (III), $C_2$–$C_3$alkyl substituted in the 2- or 3-position by methoxy, by ethoxy, by dimethylamino, by diethylamino or by a 4-morpholinyl group, and A is —O— or

with $R_4$ being hydrogen or $C_1$–$C_8$alkyl, or $X_1$ and $X_2$ are a 4-morpholinyl group or one of the groups of the formulae (Va)–(Ve) in which $R_5$, $R_6$ and $R_7$ which can be identical or different are as defined above for $R_2$, or $R_7$ is also $C_3$–$C_{11}$alkenyl or phenyl, $Q_2$ is —CO—, —CH$_2$CH$_2$— or —COCO—, p is zero or 1 and n is 1, 2, 3 or 4, and if n is 1, $X_3$ is as defined above for $X_1$ and $X_2$, and, if n is 2, $X_3$ is one of the groups of the formulae (VIa)–(VIc) in which $R_8$, $R_{10}$ and $R_{12}$ which can be identical or different are as defined above for $R_2$, or $R_8$ and $R_{10}$ are also a group of the formula (VII), $R_9$ is $C_2$–$C_8$alkylene, cyclohexylenedimethylene, methylenedicyclohexylene, phenylenedimethylene, $C_4$–$C_{10}$alkylene interrupted by a 1,4-piperazinediyl group or by 1, 2 or 3 oxygen atoms or by 1 or 2

groups, where $R_{13}$ is as defined above for $R_2$ or is aliphatic $C_1$–$C_4$acyl or ($C_1$–$C_4$alkoxy)carbonyl, or $R_9$ is also a group

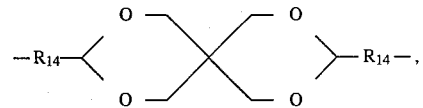

$R_{11}$ and $R_{14}$ are $C_2$–$C_4$alkylene and q is zero or 1, and, if n is 3, $X_3$ is a group of the formula (VIIIa) or (VIIIb) in which $R_{15}$, $R_{18}$, $R_{20}$, $R_{21}$, $R_{22}$ and $R_{23}$ which can be identical or different are as defined above for $R_8$ and $R_{10}$, $R_{16}$, $R_{17}$ and $R_{19}$ which can be identical or different are $C_2$–$C_4$alkylene, r and u are zero or 1 and s and t which can be identical or different are integers from 3 to 5, and, if n is 4, $X_3$ is a group of the formula (IX) in which $R_{24}$ and $R_{28}$ which can be identical or different are as defined above for $R_8$ and $R_{10}$, and $R_{25}$, $R_{26}$ and $R_{27}$ which can be identical or different are $C_2$–$C_4$alkylene, with the proviso that at least one group of the formula (II) or of the formula (VII) is present in the compounds of the formula (I).

5. A compound of the formula (I) according to claim 1, in which $X_1$ and $X_2$ which can be identical or different are a group of the formula (II), where $R_2$ is hydrogen, $C_1$–$C_{12}$alkyl, cyclohexyl or a group of the formula (III) and A is —O— or

with $R_4$ being hydrogen or $C_1$–$C_4$alkyl, or $X_1$ and $X_2$ are a 4-morpholinyl group or one of the groups of the formulae (Va)–(Ve) in which $R_5$, $R_6$ and $R_7$ which can be identical or different are as defined above for $R_2$, $Q_2$ is —CO— or —CH$_2$CH$_2$—, p is zero or 1 and n is 1, 2, 3 or 4, and, if n is 1, $X_3$ is as defined above for $X_1$ and $X_2$, and, if n is 2, $X_3$ is one of the groups of the formulae (VIa)–(VIc) in which $R_8$, $R_{10}$ and $R_{12}$ which can be identical or different are as defined above for $R_2$, or $R_8$ and $R_{10}$ are also a group of the formula (VII), $R_9$ is $C_2$–$C_6$alkylene, cyclohexylenedimethylene, methylenedicyclohexylene, $C_6$–$C_{10}$alkylene interrupted by a 1,4-piperazinediyl group or by 2 or 3 oxygen atoms or by a group

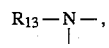

where $R_{13}$ is as defined above for $R_2$, $R_{11}$ is $C_2$–$C_3$alkylene and q is zero or 1, and, if n is 3, $X_3$ is a group of the formula (VIIIa) or (VIIIb) in which r is zero, $R_{15}$, $R_{18}$, $R_{21}$, $R_{22}$ and $R_{23}$, which can be identical or different are as defined above for $R_8$ and $R_{10}$, $R_{16}$ and $R_{17}$ which can be identical or different are $C_2$–$C_3$alkylene, u is zero or 1 and s and t which can be identical or different are integers from 3 to 5, and, if n is 4, $X_3$ is a group of the formula (IX) in which $R_{24}$ and $R_{28}$ which can be identical or different are as defined above for $R_8$ and $R_{10}$, and $R_{25}$, $R_{26}$ and $R_{27}$ which can be identical or different are $C_2$–$C_3$alkylene, with the proviso that at least one group of the formula (II) or of the formula (VII) is present in the compounds of the formula (I).

6. A compound of the formula (I) according to claim 1, in which $X_1$ and $X_2$ which can be identical or different are a group of the formula (II), where $R_1$ is hydrogen or methyl, $R_2$ is $C_1$–$C_8$alkyl, cyclohexyl, 2,2,6,6-tetramethyl-4-piperidyl or 1,2,2,6,6-pentamethyl-4-piperidyl and A is —O—, or $X_1$ and $X_2$ are a group of the formula (Va) or (Vb), in which $R_5$ and $R_6$ which can be identical or different are as defined above for $R_2$, and $R_7$ is 2,2,6,6-tetramethyl-4-piperidyl or 1,2,2,6,6-pentamethyl-4-piperidyl and n is 1, 2, 3 or 4, and, if n is 1, $X_3$ is as defined above for $X_1$ and $X_2$, and, if n is 2, $X_3$ is a group $$-\underset{R_8}{N}-(CH_2)_{2-6}-\underset{R_{10}}{N}-$$

or a group $$-N\diagup\hspace{-0.3em}\diagdown N(CH_2CH_2-\underset{R_{12}}{N})_{\overline{q}}$$

in which $R_8$, $R_{10}$ and $R_{12}$ which can be identical or different are as defined above for $R_2$ or are hydrogen, or $R_8$ and $R_{10}$ are also a group of the formula (VII), and q is zero or 1, and, if n is 3, $X_3$ is a group $$-\underset{R_{15}}{N}-(CH_2)_{2-3}-N-(CH_2)_{2-3}-\underset{R_{18}}{N}-$$

and, if n is 4, $X_3$ is a group $$-\underset{R_{24}}{N}-(CH_2)_{2-3}-N-(CH_2)_{2-3}-N-(CH_2)_{2-3}-\underset{R_{28}}{N}-,$$

with $R_{15}$, $R_{18}$, $R_{24}$ and $R_{28}$ being as defined above for $R_8$ and $R_{10}$, with the proviso that at least one group of the formula (II) or the formula (VII) is present in the compounds of the formula (I).

* * * * *